United States Patent
Kwon et al.

(10) Patent No.: US 6,940,062 B2
(45) Date of Patent: Sep. 6, 2005

(54) OPTICAL FIBER CURVATURE SENSOR FOR MEASURING BODY MOTION AND ITS ADHESIVE METHOD

(75) Inventors: Dong Soo Kwon, Taejon (KR); Kyu Bin Lee, Taejon (KR)

(73) Assignee: Korea Advanced Institute of Science & Technology, Taejon (KR)

( * ) Notice: Subject to any disclaimer, the term of this patent is extended or adjusted under 35 U.S.C. 154(b) by 0 days.

(21) Appl. No.: 09/912,357

(22) Filed: Jul. 26, 2001

(65) Prior Publication Data

US 2002/0024656 A1 Feb. 28, 2002

(30) Foreign Application Priority Data

Aug. 4, 2000 (KR) .......................... 2000-45366

(51) Int. Cl.$^7$ ................................ G01J 1/04
(52) U.S. Cl. ................................ 250/227.14
(58) Field of Search .............. 356/73.1, 512, 356/342, 121, 244, 247, 601, 521; 250/227.14–227.28, 250, 577, 231.14–231.19, 201.2, 341.1, 559.21–559.27, 214 VT, 903, 339.06–339.05; 600/595, 473, 476, 344, 436–439, 407, 310, 427, 534, 575

(56) References Cited

U.S. PATENT DOCUMENTS

| | | | | |
|---|---|---|---|---|
| 4,398,795 A | * | 8/1983 | Palmer | 156/158 |
| 4,408,495 A | * | 10/1983 | Couch et al. | 250/227.16 |
| 4,827,121 A | * | 5/1989 | Vidrine et al. | 250/227.23 |
| 5,321,257 A | * | 6/1994 | Danisch | 250/227.16 |
| 6,127,672 A | * | 10/2000 | Danisch | 250/227.14 |

* cited by examiner

Primary Examiner—Tu T. Nguyen
(74) Attorney, Agent, or Firm—Bacon & Thomas, PLLC

(57) ABSTRACT

An adhesive method for an optical fiber curvature sensor results in a sensor having improved sensitivity for measuring body motions such as motions of fingers, arms, or legs, and in particular that is capable of measuring both a curving direction and degree of curvature of a subject simultaneously, even for variable surface areas such as those of the waist or shoulders. The method is carried out by adhering an optical fiber to a subject in a curved state.

1 Claim, 5 Drawing Sheets

OPTICAL FIBER CURVATURE SENSOR FOR MEASURING BODY MOTION AND ITS ADHESIVE METHOD

BACKGROUND OF THE INVENTION

1. Field of the Invention

The present invention relates to an optical fiber curvature sensor for measuring body motion and its adhesive method. More particularly, it relates to an optical fiber curvature sensor for measuring body motion and its adhesive method having an improved sensitivity for measuring body motions such as motions of fingers, arms, or legs, which is able to measure curving direction and curved degree of a subject simultaneously and applicable for subjects of which the surface areas are varying such as waist or shoulders, by adhering an optical fiber to a subject in curved-state.

2. Description of the Related Art

In the prior art related to an optical fiber curvature sensor for measuring body motion, a method for measuring motions of fingers, arms, or legs, which uses the fact that the characteristic of light through an optical fiber is changed when the optical fiber is bent, is disclosed in U.S. Pat. No. 4,542,291 ("Optical Flex Sensor", patented Sep. 17, 1985, Thomas G. Zimmerman, VPL Research Inc.). In addition, a glove-type hand motion measuring device having various sensors is disclosed in U.S. Pat. No. 4,414,537 ("Digital Data Entry Glove Interface Device", patented Nov. 8, 1983, Gary J. Grimes, Bell Telephone Lab. Inc.), and glove-type hand motion measuring devices having optical fiber curvature sensors have been developed thereafter (General Reality Company).

Additionally, an optical fiber curvature sensor is also used for measuring angles of arms or legs of which the articulations have one degree of freedom. Moreover, by laminating optical fibers having one degree of freedom, an optical fiber curvature sensor that can measure a 3-D shape in 3-D space has been developed (Measurand Inc.).

However, the optical fiber curvature sensors in the prior art described above are limited to measuring motions of subjects having small surface area variances such as fingers. Therefore, it is hardly applicable for measuring motions of subjects having large surface area variances such as waist or shoulders.

And, there exists another problem that the measuring devices for body motion in the prior art are very expensive because they are manufactured by using a high-price magnetic position sensor and/or a high-price image processing technique.

SUMMARY OF THE INVENTION

The present invention is proposed to solve the problems of the prior art mentioned above. It is therefore the object of the present invention to provide an optical fiber curvature sensor for measuring body motion and its adhesive method having an improved sensitivity for measuring body motions such as motions of fingers, arms, or legs, which is able to measure curving direction and curved degree of a subject simultaneously and applicable for subjects of which the surface areas are varying such as waist or shoulders, by adhering an optical fiber to a subject in curved-state. It is another objective of the present invention to provide an optical fiber curvature sensor and its adhesive method, which is applicable for developing a low-price measuring device for body motion.

To achieve the object mentioned above, the present invention presents an optical fiber curvature sensor for measuring body motion comprising a light source emitting a light, an optical fiber, comprising an inside core and an outside clad in a cylindrical shape, connected to the light source by a connector at an end, and a light receiving element, measuring the intensity of light transmitting through the optical fiber, connected to the optical fiber by a connector at the other end, wherein some portion of the clad is eliminated by heat treatment and a cutout-groove is formed thereon.

The present invention also presents an adhesive method of an optical fiber curvature sensor for measuring body motion comprising a light source emitting a light, an optical fiber, comprising an inside core and an outside clad of which some portion is eliminated by heat treatment and a cutout-groove is formed thereon, connected to the light source by a connector at an end, and a light receiving element, measuring the intensity of light transmitting through the optical fiber, connected to the optical fiber by a connector at the other end, characterized by adhering an optical fiber to a subject in curved-state.

Figure 1:
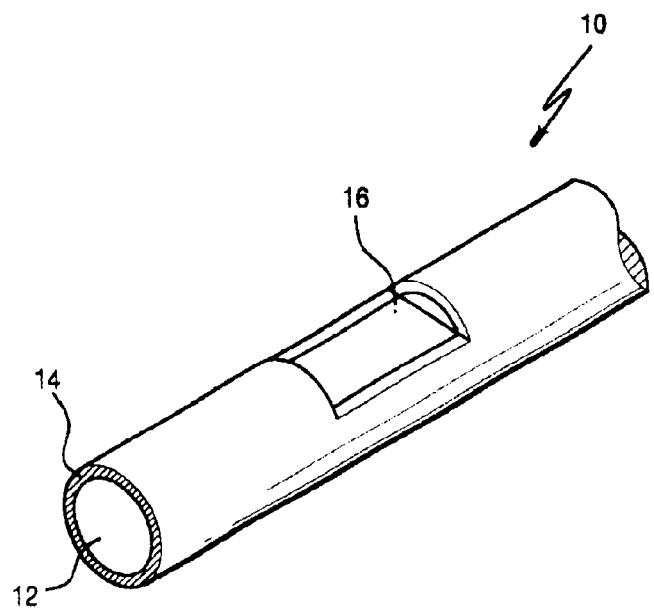
FIG. 1 is a perspective view of an optical fiber in accordance with the present invention.
Figure 2:
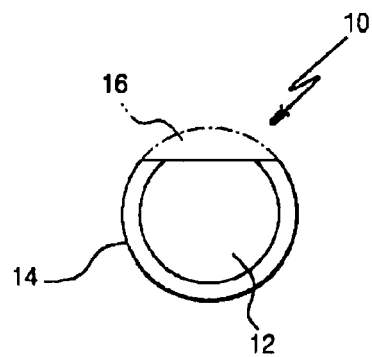
FIG. 2 is a cross-sectional view of an optical fiber in accordance with the present invention.

<Description of the Numerals on the Main Parts of Drawings>

10: an optical fiber
12: a core
14: a clad
16: a cutout-groove
20: a light source
30a, 30b: connectors
40: a light receiving element
50: a subject
60: an optical fiber curvature sensor

DETAILED DESCRIPTION OF THE EMBODIMENTS

An optical fiber curvature sensor for measuring body motion in accordance with the present invention comprises a light source emitting a light, an optical fiber of which the clad is heat-treated to improve sensitivity and detect curving direction, a light receiving element measuring the intensity of light transmitting through the optical fiber, a connector connecting the light source and the optical fiber, and another connector connecting the optical fiber and the light receiving element.

Hereinafter, referring to appended drawings (FIG. 1–FIG. 9), the structures and the operation procedures of the embodiments of the present invention are described in detail.

Looking into the basic structure of an optical fiber curvature sensor for measuring body motion in accordance with the present invention, it comprises a light source (20) emitting a light, an optical fiber (10), comprising an inside core (12) and an outside clad (14) in a cylindrical shape, connected to the light source (20) by a connector (30a) at an end, and a light receiving element (40), measuring the intensity of light transmitting through the optical fiber (10), connected to the optical fiber (10) by a connector (30b) at the other end, wherein some portion of the clad (14) is eliminated by heat treatment and a cutout-groove (16) is formed thereon.

An embodiment of an optical fiber curvature sensor (60) in accordance with the present invention is now described in detail.

An optical fiber (10) comprises a core (12) having high refractive index and a clad (14), having relatively low refractive index, surrounding the core (12). Therefore, in case that the refractive index $(n_1)$ of core (12) is higher than the refractive index $(n_2)$ of clad (14) (i.e., $n_1 > n_2$), a light incident at an end of an optical fiber (10) remains inside the core (12) and transmits to the other end of the optical fiber (10) by means of total reflections repeatedly occurring at the boundary between core (12) and clad (14).

The present invention eliminates some portion of clad (14) of an optical fiber (10) by heat treatment to form a cutout-groove (16) thereon so that it can detect curving direction of a subject as well as improve sensitivity.

For example, a plastic optical fiber (10) of 1 mm diameter is partially heated by 200° C.–430° C. and 0.2 mm of clad (14) is eliminated.

Figure 3:
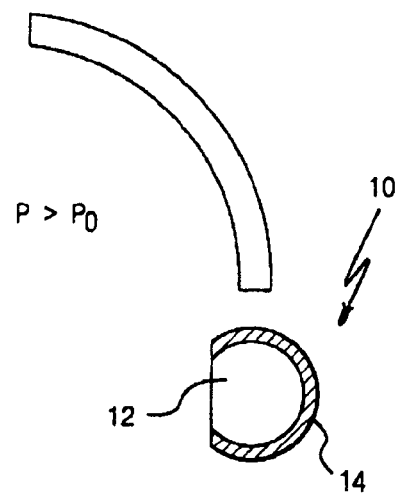
FIG. 3 is a view illustrating the sensing principle of an optical fiber in accordance with the present invention.
Figure 4:
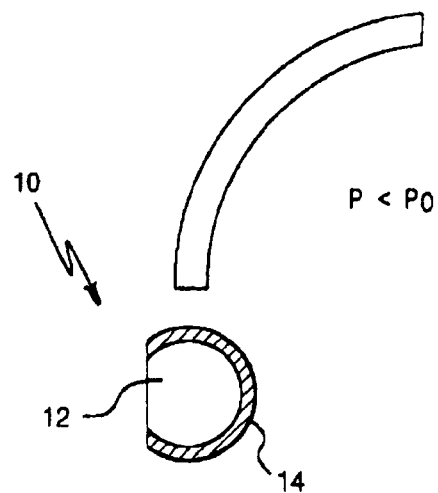
FIG. 4 is another view illustrating the sensing principle of an optical fiber in accordance with the present invention.

Referring to FIG. 3, in case that an optical fiber (10) of which some portion of clad (14) is eliminated is curved to heat-treated direction, the amount of transmitted light (P) is larger than the amount of transmitted light $(P_0)$ under the straight condition (i.e., $P > P_0$). And, referring to FIG. 4, in case that the optical fiber (10) is curved opposite to heat-treated direction, the amount of transmitted light (P) is smaller than the amount of transmitted light $(P_0)$ under the straight condition (i.e., $P < P_0$).

In other word, in case that an optical fiber (10) is curved to the direction where some portion of clad (14) is eliminated by heat treatment, the intensity of light transmitting through the optical fiber (10) increases, and in case that an optical fiber (10) is curved to the opposite direction where some portion of clad (14) is eliminated, the intensity of light transmitting through the optical fiber (10) decreases. Thus, by using an optical fiber (10) of which some portion of clad (14) is eliminated, curving direction and curved degree can be measured at the same time, and the sensitivity improves because the light intensity variance due to curvature is increased.

Figure 5:
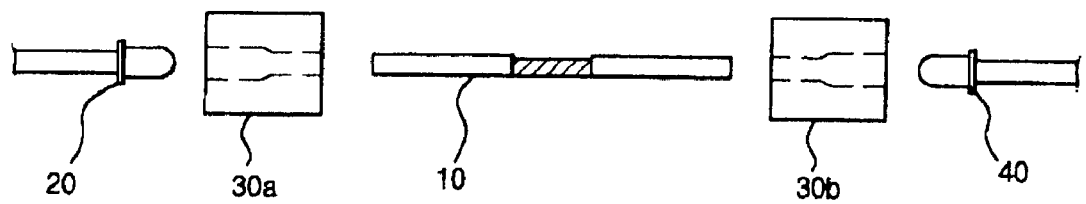
FIG. 5 is a lateral view of an optical fiber curvature sensor in accordance with the present invention before being assembled.
Figure 6:
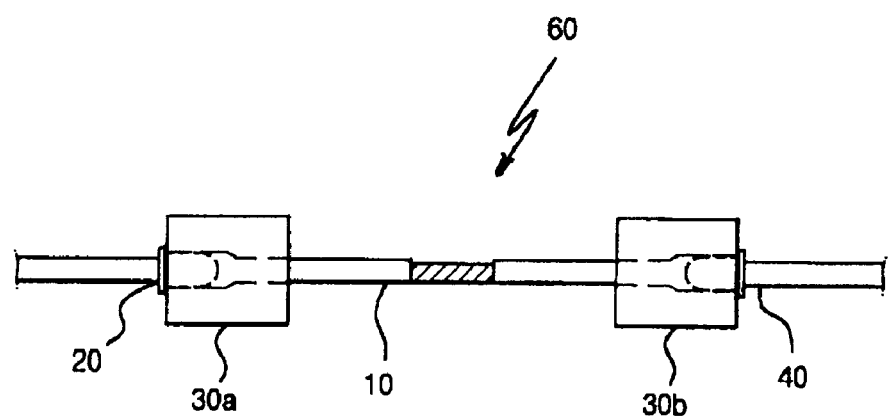
FIG. 6 is a lateral view of an optical fiber curvature sensor in accordance with the present invention after being assembled.

To assemble an optical fiber curvature sensor (60) using an optical fiber (10) described above, the optical fiber (10) has to be connected to a light source (20) emitting a light and to a light receiving element (40) measuring the intensity of light transmitting through the optical fiber (10) as described in FIG. 5 and FIG. 6. These connections are performed by using connectors (30a, 30b).

In other words, an optical fiber curvature sensor (60) in accordance with the present invention comprises a light source (20) emitting a light, an optical fiber (10) of which some portion of clad (14) is eliminated by heat treatment to improve sensitivity and detect curving direction, a light receiving element (40) measuring the intensity of light transmitting through the optical fiber (10), a connector (30a) connecting the light source (20) to an end of the optical fiber (10), and another connector (30b) connecting the light receiving element (40) to the other end of the optical fiber (10). Here, a general LED can be used as a light source (20), however, an infrared LED is desirable for being less effected by external light.

A general phototransistor is used as a light receiving element (40) and it is desirable to use the most sensitive one to the wavelength of the light emitted from the light source (20).

In case of an optical fiber curvature sensor (60) described above being adhered to a subject (50) of which the curvature is to be measured, the sensor (60) is adhered to the subject (50) with optical fiber (10) being curved before being adhered so that it can measure the curvature of the subject (50) even if its surface area varies.

Figure 7:
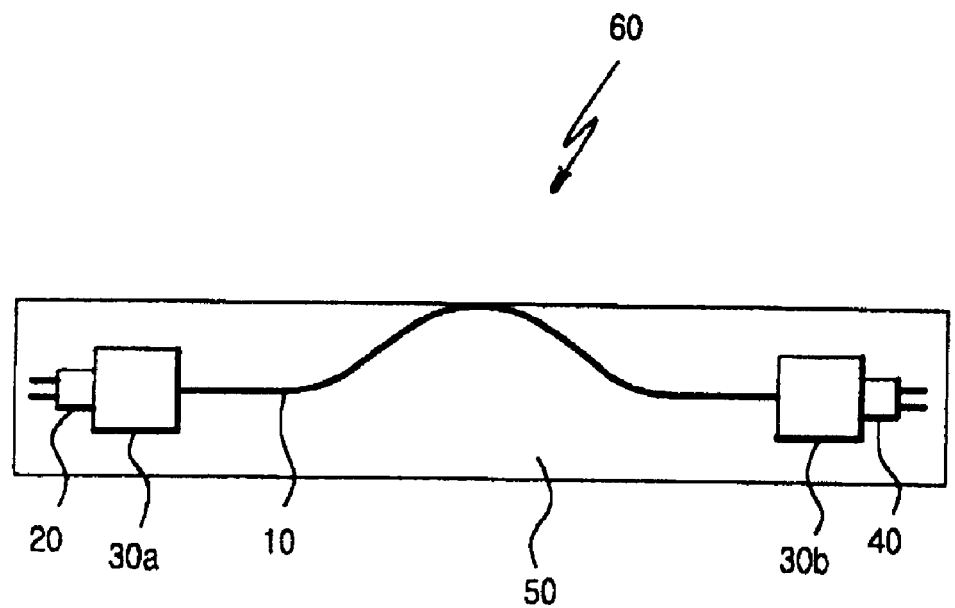
FIG. 7 is a view illustrating an adhesive state of an optical fiber curvature sensor in accordance with the present invention.
Figure 8:
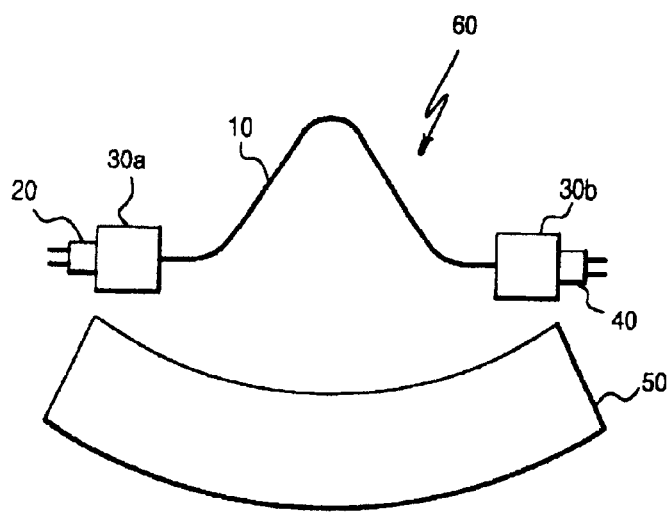
FIG. 8 is a view illustrating the change in curved state of an optical fiber according to the bent of a subject.

In other words, after an optical fiber curvature sensor (60) is adhered to a straight subject (50) with optical fiber (10) being curved as shown in FIG. 7, if the subject (50) is bent in the direction where optical fiber curvatures sensor (60) is adhered as shown in FIG. 8, the optical fiber (10) comes to be curved more than its initial state and thus, the amount of light transmitting through the optical fiber (10) is varied and the intensity of light measured by the light receiving element (40), one can notice that the curving direction of the subject (50) is downward in this case, and by checking the amount of intensity change of the light, one can measure the curved degree of the subject (50).

Figure 9:
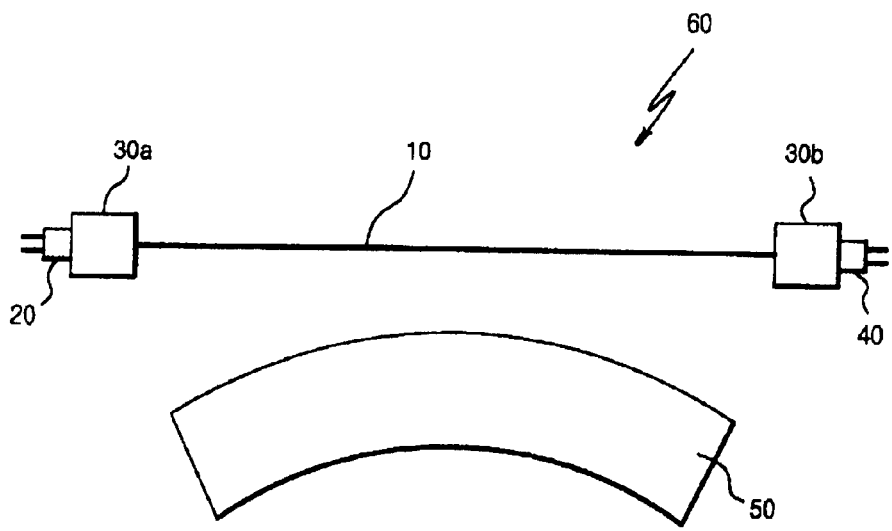
FIG. 9 is another view illustrating the change in curved state of an optical fiber according to the bent to subject.

Or, after an optical fiber curvature sensor (60) is adhered to a straight subject (50) with optical fiber (10) being curved as shown in FIG. 7, if the subject (50) is bent in the opposite direction where the optical fiber curvature sensor (60) is adhered as shown in FIG. 9, the optical fiber (10) comes to be curved less than its initial state and thus, the amount of light transmitting through the optical fiber is varied thereby. Therefore, by checking the intensity of light measured by the light receiving element (40), one can notice that the curving direction of the subject (5) is upward in this case, and by checking the amount of intensity change of the light, one can measure the curved degree of the subject (50).

As described above, an optical fiber curvature sensor in accordance with the present invention, which is applicable for measuring the curvature of a subject of which the surface area is varying like human body, improves the sensitivity of an optical fiber by heat treatment and measures curving direction and curved degree of a subject simultaneously by using a single optical fiber curvature sensor.

In addition, an optical fiber curvature sensor in accordance with the present invention has simple structure and is applicable for measuring the curvature of a subject, of which the surface area is varying, by following a simple adhesive method. Since an optical fiber curvature sensor in accordance with the present invention is applicable for measuring motions of body parts, of which the surface areas vary much when they are in motion, such as shoulders, waist, or legs, it can be applicable for developing a measuring device for whole body motion.

And, the present invention presents a low-price optical fiber curvature sensor for measuring body motion. Thus, it can be competitively applicable for industries such as animation and/or game industries.

As mentioned thereinbefore, the present invention presents an optical fiber curvature sensor for measuring body motion having an improved sensitivity for measuring body motions such as motions of fingers, arms, or legs, which is able to measure curving direction and curved degree of a subject simultaneously and applicable for subjects of which the surface areas are varying such as waist or shoulders, by adhering an optical fiber to a subject in curved-state. The optical fiber curvature sensor in accordance with the present invention is applicable for developing a low-price measuring device for body motion.

Since those having ordinary knowledge and skill in the art of the present invention will recognize additional modifications and applications within the scope thereof, the present invention is not limited to the embodiments and drawings described above.

What is claimed is:

1. An adhesive method for an optical fiber curvature sensor that includes:

a light source (20) for emitting a light;

an optical fiber (10) having first and second ends, comprising an inside core (12) and an outside clad (14) of which some portion is eliminated by heat-treatment and in which a cutout-groove (16) is formed, said optical fiber being connected to said light source (20) at the first end; and a light receiving element (40) for measuring the intensity of light transmitting through said optical fiber (10) and connected to said optical fiber (10) at the second end, said method comprising the steps of:

adhering said optical fiber (10) to a subject (50) bendable body part when said subject body part is in a curved state; and measuring a degree of curvature of said body part and simultaneously determining a direction of said curvature based on said intensity of light measured by the light receiving element.

* * * * *